United States Patent [19]

Nishino et al.

[11] 4,071,636
[45] Jan. 31, 1978

[54] METHOD OF PRODUCING SHEET-FORMED BACTERICIDAL ARTICLE

[75] Inventors: Atsushi Nishino; Kazunori Sonetake; Hiroshi Kumano, all of Kadoma, Japan

[73] Assignee: Matsushita Electric Industrial Co., Ltd., Japan

[21] Appl. No.: 595,229

[22] Filed: July 11, 1975

Related U.S. Application Data

[63] Continuation-in-part of Ser. No. 414,134, Nov. 8, 1973, abandoned.

[30] Foreign Application Priority Data

| Feb. 14, 1973 | Japan | 48-18789 |
| Nov. 9, 1972 | Japan | 47-112698 |
| Nov. 9, 1972 | Japan | 47-112695 |
| Nov. 9, 1972 | Japan | 47-112691 |

[51] Int. Cl.² .................................... B01D 39/08
[52] U.S. Cl. ........................................ 427/2; 210/501; 427/244
[58] Field of Search ................. 210/501, 266, 500 M; 427/2, 404, 244; 55/16; 96/114

[56] References Cited

U.S. PATENT DOCUMENTS

| 1,744,281 | 1/1930 | Pfiffner ........................... 427/404 X |
| 2,785,106 | 3/1957 | Mendelsohn .................... 210/501 X |
| 2,791,518 | 5/1957 | Stokes, Jr. et al. ................. 427/2 X |
| 3,058,845 | 10/1962 | Hendricks ........................... 117/160 |
| 3,091,554 | 5/1963 | Rosser et al. ....................... 117/160 |
| 3,276,996 | 10/1966 | Lazare ........................ 210/500 M X |
| 3,327,859 | 6/1967 | Pall ...................................... 210/266 |
| 3,342,729 | 9/1967 | Strand .................................. 55/16 X |

Primary Examiner—Frank A. Spear, Jr.

[57] ABSTRACT

A sheet of partially acetalled polyvinyl alcohol is used as the substratum of the article, and a sparingly soluble silver halide is precipitated on the sheet from an aqueous phase such as an ammoniacal silver chloride solution.

6 Claims, 9 Drawing Figures

METHOD OF PRODUCING SHEET-FORMED BACTERICIDAL ARTICLE

This application is a continuation-in-part of Ser. No. 414,134 filed Nov. 8, 1973, now abandoned.

The present invention relates to a method of producing a sheet-formed bactericidal article which is useful for sterilizing water in water purifying devices.

Various types of water purifiers are currently on the market for use in homes and shopss to deodorize and improve the taste of city water or any other potable water. Most of them are designed to remove chlorine or bleaching powder from the potable water supplied thereto by means of an absorbent such as activated carbon. The thus dechlorinated water no longer has any bactericidal power, and it is feared that bacteria including pathogenic and coliform ones may propagate in the reservoir section and discharge pipe of the water purifier if extreme care is not taken in operation and maintenance of the purifier and/or the purifier is left unused for a few days. To prevent such contamination of the dechlorinated water, it has been proposed to employ a bactericidal filter which is coated and/or impregnated with a bactericide as typified by silver chloride in the described type of water purifier.

In practical applications, however, some problems arise when a filter is coated with silver chloride. Firstly, deposition of silver chloride on the filter inevitably chokes the pores of the filter to some extent and impairs filtering efficiency. Next, accumulation of activated carbon on the filter has an adverse effect on the bactericidal ability of silver chloride for the following reason. Since activated carbon absorbs and carries chlorine ion, the chlorine ion concentration around the filter increases as more activated carbon particles accumulate on the filter, and the resulting common-ion effect strongly inhibits the dissolution of silver chloride into the dechlorinated water. Consequently, the filter retains its bactericidal ability only for a relatively short period of time in the beginning of its practical use. Besides, it is quite difficult to coat and/or impregnate usual filter materials with silver chloride particles thus impairing success in meeting fundamental requirements such as high adhesion strength, uniform distribution and adequate dissolution rate of the deposited particles. It is impossible to give a constant silver ion concentration in the treated water unless these requirements are met satisfactorily.

If silver chloride is not deposited on the filter but directly mixed with or absorbed in the activated carbon, there will arise additional disadvantages such as separation of silver chloride from the activated carbon with resultant sedimentation of the former due to the great difference in their specific gravities, and/or difficulty in maintaining the silver ion concentration in the treated water at an appropriate level.

It is an object of the present invention to provide a method of producing a bactericidal article for the sterilization of drinking water, which article is applicable to various types of water purifiers and more effective in bactericidal function than bactericidal filters of the prior art.

It is another object of the invention to provide a method of producing a sheet-formed bactericidal article which is coated with uniformly distributed and strongly adhering fine particles of a silver halide and exhibits a constant and long-lasting sterilizing ability in flowing water.

It is another object of the invention to provide a method of producing the described bactericidal article, which method is simple, economical and suitable for production in large quantity and uniform quality.

According to a method of the invention, a sheet of partially acetalled polyvinyl alcohol is utilized as the substratum sheet of the bactericidal article and a silver halide selected from the chloride, bromide and iodide is precipitated on the sheet from an aqueous liquid phase.

In one aspect of the invention, a substratum sheet of the described material is initially soaked in an aqueous solution of a soluble silver compound and then soaked in an aqueous solution of a soluble halide followed by washing with water and drying. In another and more preferred aspect of the invention, a substratum sheet of the described material is soaked in an aqueous ammoniacal silver halide solution followed by drying.

Other features and advantages of the invention will become apparent from the following detailed description of preferred embodiments thereof with reference to the accompanying drawings, in which:

We consider that the best way to prevent propagation of bacteria in a water purifier which has an absorbent for dechlorination of potable water is to dispose a suitably shaped bactericidal article in the water purifier at a section between a filter for filtering out the absorbent and the outlet port. Such disposition of the bactericidal article in the water purifier allows the filter to be free from any bactericide coating which is obstructive of its principal filtering function and does not allow the chlorine ion which is absorbed in and carried by the absorbent to concentrate around the bactericide.

In selecting a bactericidal agent for such an article, some factors such as solubility in water, influences on human health and the taste and odor of the treated water must be taken into consideration besides the bactericidal ability, and sparingly watersoluble silver compounds are known for their satisfactory properties in these respects. Particularly, three kinds of silver halides, namely, chloride, bromide and iodide, are favored for their adequate solubilities in water, which are $10^{-5}$, $10^{-6}$ and $10^{-8}$, respectively. In the present invention, any of these three silver halides can be used as a bactericidal agent, and silver chloride is most preferred in view of its solubility and production costs.

The selected silver halide must be coated on or involved in a certain base material to prevent it from being dispersed in and carried away by the treated water when disposed in a water purifier at a section downstream of a filter. In the present invention, the base material is sheet-formed for obtaining the largest effective surface area with a minimum quantity of the silver halide. The sheet-formed material is preferably porous so that the effective surface area is further increased. A bactericidal article according to the invention is not expected to serve as a filter, but porosity of the sheet-formed material is desirable for avoiding a significant resistance to the flow of water in the purifier. In addition, the sheet-formed material is preferably soft and flexible so that the end product, i.e., the bactericidal article, may be easily and freely formed into a three-dimensional shape best suited to each type of water purifier. Accordingly, various types of fabrics or cloths are practical and examples of the sheet-formed material in the invention. Either relatively fine cloths, e.g. for clothing uses, or coarse and canvaslike cloths can be used, and both the woven and non-woven cloths are useful. In general, the use of a non-woven cloth brings about best results.

A decisive factor in the production of a bactericidal article for the described use is the material of the substratum sheet. The material must naturally be insoluble in water and chemically stable in the wet state since silver halides have strong corrosive properties. Physical strength, durability in water and resistance to funguses are also important properties to be taken into consideration. Furthermore, it is absolutely necessary that the material is adequately hydrophilic and water-wettable because the silver halide is precipitated on the substratum sheet from an aqueous medium as will be described hereinafter. The last requirement is quite important for obtaining a bactericidal article for use in a water purifier. A bactericidal article according to the invention is a vinylon sheet coated and in most cases also impregnated with extremely fine particles of a silver halide. These particles are expected to dissolve in water at a slow rate when the article is kept in water since a low silver ion concentration in water suffices to ensure the sterilization of water and suits drinking water. It is undesirable that the solid particles of the silver halide separate from the article and disperse in water because of the resulting shortening of the life of the article and presence of the particles in the "purified" water.

We have found that adhesion strength of the silver halide particles are greatly governed by the material of the substratum sheet and that an exceptionally excellent result can be obtained by the use of vinylon, which is a common name in Japan for partially acetalled polyvinyl alcohol and called vinal in the U.S.A., as the material. Vinylon is used preferably in the form of cloth as described above, but also a porous film may be used.

It seems that synthetic resins of fibers generally meet the above described fundamental requirements for the sheet material to produce the described article. We have found, however, that vinylon is the only polymer that can satisfy all the requirements. The advantages of vinylon over other types of synthetic fibers and natural fibers are primarily attributable to its chemical structure.

Vinylon is fundamentally polyvinyl alcohol, which is produced by hydrolysis of polyvinyl acetate. Polyvinyl alcohol itself is soluble in water but becomes insoluble when acetal groups are formed with some of its hydroxyl groups by partial condensation with an aldehyde. The thus partially acetalled or acetalformed polyvinyl alcohol is called vinylon, the structure of which is represented by If the condensation is completed, the resulting polymer is no longer called vinylon but a polyvinyl acetal. In general, there is no definite limit of the extent to which the acetal formation is carried out. In the present invention, however, the extent of acetal formation is restricted to less than 50 mole % and preferably in the range between 5 and 30 mole %, so that vinylon retains hydroxyl groups in numbers large enough to render the polymer hydrophilic and fully wettable. The excellent wettability of vinylon is a primary cause for the fact that the silver halide particles adhere uniformly and strongly on a vinylon sheet. If the acetal formation is performed to the extent of 50 mole %, the polymer cannot be made filamentous but rather only in the form of flocculent and ragged fibrous material. An additional advantage of vinylon resides in that vinylon is one of the cheaper synthetic fibers.

Among other synthetic fibers, polyamides (typified by nylon), polyesters such as polyethylene terephthalate (Dacron) and polyacrylonitrile (Orlon) are excellent in chemical stability and physical strength, but they are inferior to vinylon in their affinity to water or wettability and hence in their ability to strongly retain a uniform coating of a silver halide thereon. The wettability is usually governed by the ratio of the number of hydrophilic groups of a polymer to the number of carbon atoms in the chain. The superiority of vinylon in this respect can be understood from the comparison of the above structure with the following structures of the other three polymers From a practical viewpoint, vinylon is comparable with nylon and polyesters in physical strength and resistances to water, acids, heat and funguses.

As to the affinity to water, rayons which are generally represented by $(C_6H_9O_4(OH))_n$ are comparable with and sometimes superior to vinylon. Accordingly it is quite easy to form a silver halide coating of satisfactory qualities on a rayon fabric. Rayons are, however, easily attacked by various chemicals and funguses. Besides, rayon fabrics absorb water too much and swell noticeably when left in water for a long period of time. Since the swelling results in significant reduction in the physical strength of the fabric, rayons are not practical for the purpose of the invention.

Natural fibers as typified by cotton are represented by a simplified formula $(C_6H_{10}O_5)_n$. They are highly wettable like rayons since they have hydroxyl groups, but easily attacked by funguses and bacteria when kept in water for a long period of time due principally to their large number of hydrogen atoms compared with the number of carbon atoms. Furthermore, natural fibers are easily affected by chemicals such that they are weakened even by chemical treatments to form a silver halide coating thereon.

In the present invention, vinylon is used preferably alone, but it is permissible to use a blend of vinylon with another synthetic fiber such as nylon, a polyester, or polypropylene.

Figure 1:
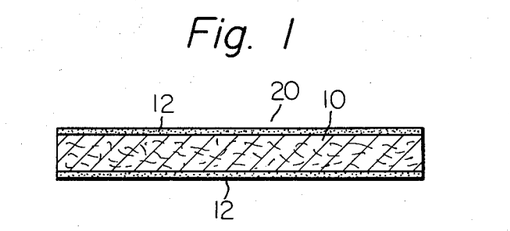
FIG. 1 is a schematic sectional view of a sheet-formed bactericidal article produced by a method according to the invention.

Referring now to the drawings, FIG. 1 shows schematically and sectionally an example of bactericidal articles produced according to a method of the invention. In this example, a sheet of non-woven vinylon cloth 10 is used as the porous substratum of a sheet-formed bactericidal article 20, and a coating 12 of a silver halide is formed on each side of the cloth 10. The width and length of the cloth 10 do not matter particularly since the bactericidal sheet 20 can be cut into pieces of desired sizes in accordance with particulars of the water purifier in which the bactericidal sheet 20 is to be disposed. The thickness of the cloth 10, however, affects the properties of the bactericidal sheet 20 and preferably ranges from 0.01 to 5 mm depending on the type of the cloth 10 and the intended use of the bactericidal sheet 20. There arises no significant difficulty in the production of the bactericidal sheet 20 even if the thickness of the cloth 10 exceeds 5 mm, but such a large thickness leads to the following disadvantages of the product in use. In addition to occupying greater space in a water purifier, the excessively thick bactericidal sheet 20 offers a significant resistance against the flow of water and disturbs dissolution of the coated silver halide and diffusion of silver ions into the water. If the cloth 10 is thinner than 0.01 mm, on the other hand, the bactericidal sheet 20 cannot have a satisfactory physical strength to withstand changes in water pressure and various external shocks inflicted during prolonged use in water.

As to the silver halide coating 12, the thickness may be determined in accordance with external factors such as the construction of the water purifier with which the bactericidal sheet 20 is to be used and the quality of the water. In general, however, the thickness of the coating 12 is preferably in the range between 0.004 and 50 microns. Thicker coatings 12 will hinder the flow of water passing through the bactericidal sheet 20 and cause an increase in production costs. On the other hand, coatings 12 which are thinner than 0.004 microns will be exhausted by dissolution in an unduly short time compared with the life of, for example, activated carbon in the same water purifier.

Figure 2:
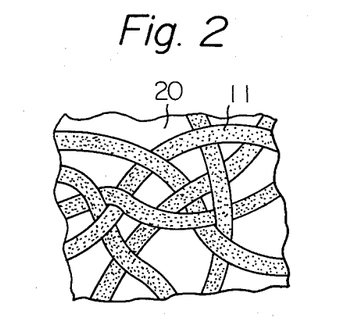
FIG. 2 is a schematic and enlarged plan view of the same article.
Figure 3:
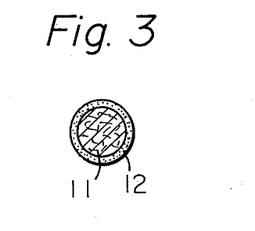
FIG. 3 is a schematic and enlarged cross-sectional view of a single fiber filament constituting the sheet of FIG. 1.

The coatings 12 are preferably formed in a porous state so as to allow water to pass through the bactericidal sheet 20. When the vinylon substratum 10 of the bactericidal sheet 20 is of a cloth fabric, which may be either woven or non-woven, as in this example, the cloth 10 usually is not only coated but also impregnated with the silver halide. Since the particle size of the silver halide 12 precipitated according to a method of the invention is extremely small, pores of the cloth 10 or interstices of fiber filaments are left vacant at least partly as shown in FIG. 2, wherein each filament is indicated at 11. Each filament 11 can be coated with the silver halide 12 over almost the entire surface thereof as shown in FIG. 3.

The silver halide particles of the coatings 12 easily separate from the cloth 10 if the coatings 12 are formed by a direct application of the silver halide in the solid form, for example, by the application of a dispersion of the silver halide particles in a liquid medium. It is impossible to use an aqueous solution which is concentrated enough to give the coatings 12 a satisfactory thickness and denseness.

According to the invention, a sparingly soluble silver halide is precipitated on the vinylon substratum 10 from an aqueous liquid phase so that the coatings 12 may be formed of extremely fine particles of the silver halide which adhere to the cloth 10 with high adhesive strength and uniform distribution.

Figure 4:
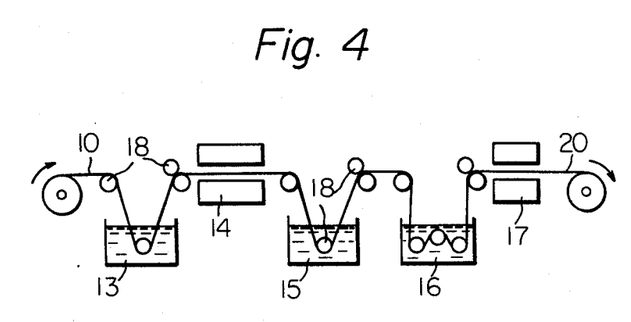
FIG. 4 is a flow diagram showing one aspect of a method according to the invention.

A first embodiment of a method according to the invention will be described with reference to FIG. 4. As described previously, silver chloride, silver bromide and silver iodide are useful for forming the bactericidal coating 12, but silver chloride alone will be mentioned in the description hereinafter as a typical and most practical example.

A rolled belt of the porous vinylon sheet 10 is at first immersed in an aqueous solution 13 of a water soluble silver compound, which is preferably silver nitrate. The concentration of silver nitrate in the solution 13 is adjusted to remain in the range between 1 to 20% by weight. If the concentration is below 1%, the vinylon sheet 10 is coated and impregnated with silver nitrate only in an insufficient quantity. When the concentration is above 20%, the solution 13 does not easily wet the surfaces of the sheet 10 so as to give dense and close coatings of silver nitrate when the wet sheet 10 is dried subsequently. Besides, the excessively concentrated solution 13 does not soak into the sheet 10 especially well when the sheet 10 is a relatively thick one and/or of a fabric with a fine texture.

After withdrawal from the solution 13, the wet sheet 10 is dried in a dryer 14. Although the drying is not an essential requisite, it is preferable to remove water at this stage because dehydration is effective both in increasing the adhesive strength of the coatings 12 and improving the utilization efficiency of silver ions in the solution adhering to the sheet 10. Then the dried sheet 10 is passed through an aqueous solution 15 of a water soluble halide as exemplified by sodium chloride to convert the adhering silver nitrate into silver chloride. Since silver halides are sparingly soluble in water, the halogenation of the adhering silver nitrate is easily accomplished in a solution 15 having low halogen concentration. The reaction occurs even when the halogen concentration in the solution 15 is as small as 500 ppm and proceeds at an adequate rate when the concentration is at least 1%. If the solution 15 is too concentrated only the outer surfaces of the silver nitrate particles will be halogenated, leaving the inner portions unchanged. After removal from the sodium chloride solution 15, the wet sheet 10 which is now coated with silver chloride is washed with water 16, dried in a second dryer 17 and finally rolled up as a finished bactericidal sheet 20. The entire process can be performed continuously by conveying the belt of the vinylon sheet 10 by the aid of rollers 18.

This method features simplicity both in apparatus and operation and silver chloride coatings 12 having an adequate porosity, uniform thickness and high adhesive strength. Furthermore, the thickness of the coatings 12 can be controlled precisely by adjusting the concentrations of the two solutions 13 and 15 and immersion times in these solutions. This method is especially suitable for the production of relatively thin bactericidal coatings 12.

Figure 6:
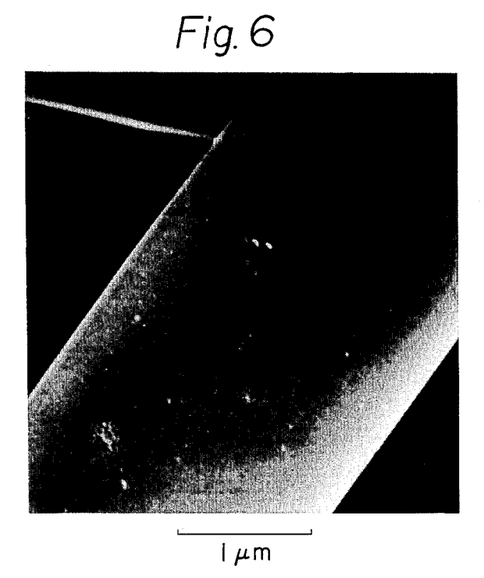
FIG. 6 is a scanning electron micrograph of a nonwoven cloth of vinylon which is used as a substratum sheet for the bactericidal sheet of FIG. 1.
Figure 7:
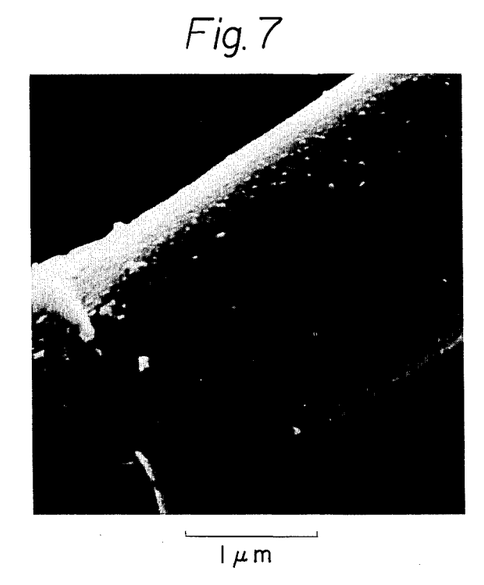
FIG. 7 is a scanning electron micrograph of the bactericidal article of FIG. 1 produced by the use of the vinylon cloth of FIG. 6.

FIG. 6 is a scanning electron micrograph of a non-woven cloth of vinylon. The photograph is of 3000 magnification, and the cloth is not yet coated with any bactericide. The electron micrograph of FIG. 7 is of the same vinylon sheet after it has been cessed by the above described procedures, and extremely fine particles of silver chloride are observed on the surface of a single vinylon filament with a suitable uniform distribution.

Figure 8:
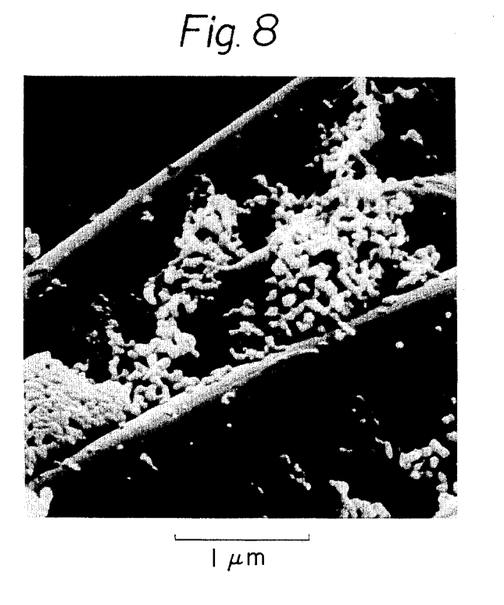
FIG. 8 is a scanning electron micrograph of a nylon cloth, on which are deposited silver chloride particles.
Figure 9:
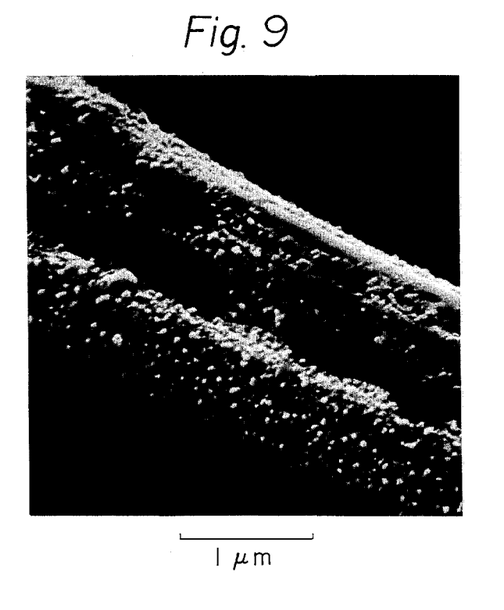
FIG. 9 is a similar micrograph for a rayon cloth.

FIG. 8 is a similar electron micrograph obtained for a nylon cloth which has been subjected to the same coating process. In this case, silver chloride particles have apparently larger particle sizes and accumulate locally. It appears that these particles do not adhere strongly to each nylon filament. FIG. 9 is a similar electron micrograph for rayon. Each filament is uniformly coated with fine particles of silver chloride in larger quantities than in the case of vinylon. Despite such excellence in the physical properties of the bactericidal coating formed on rayon fibers, the above described shortcomings of rayon itself render any rayon fabric useless in the production of the bactericidal article for water purifiers.

Figure 5:
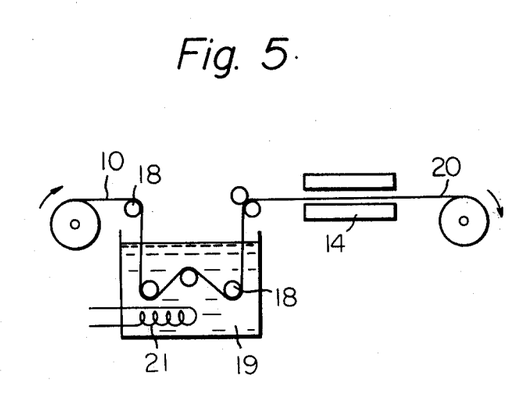
FIG. 5 is a flow diagram showing another aspect of a method according to the invention.

According to a second embodiment of the invention, the same porous vinylon sheet 10 as in the above embodiment is used, but a silver halide, e.g. silver chloride, is precipitated on the vinylon sheet from a silver complex solution. As shown in FIG. 5, the vinylon sheet 10 is immersed in a silver ammine complex solution 19 which is prepared by dissolving silver chloride in an aqueous ammonia. The concentration of silver chloride in this aqueous ammoniacal solution 19 can be varied within the range between 0.1 and 20% by weight depending on the type and thickness of the vinylon sheet 10. The initial aqueous ammonia is of a concentration ranging from 1 to 28% by weight.

A silver chloride content of less than 0.1% is insufficient for forming coatings 12 having the necessary thickness by a single step. It is difficult to prepare an ammoniacal solution containing silver halide dissolved therein in an amount of more than 20%. In general it becomes increasingly difficult to obtain a dense and close silver chloride coating 12 when the silver chloride concentration in the ammoniacal solution 19 approaches 20%. Accordingly, the silver chloride concentration must be determined very carefully especially when a relatively high concentration is employed for the purpose of forming a coating 12 having a relatively large thickness.

The concentration of the starting aqueous ammonia is varied within the aforementioned range depending on the intended silver chloride concentration in the final solution 19 since the solubility of silver chloride in an aqueous ammonia solution is proportional to the ammonia concentration in correlation with the temperature. The ammonia concentration is preferably limited to 14% at the maximum. When a higher ammonia concentration is employed, it becomes necessary to keep the solution 19 in a pressurized chamber or alternatively to cool it by the use of apparatus of a large capacity so that the evaporation of ammonia may be reduced as much as possible, because aqueous ammonia has a relatively high vapor pressure even at room temperature. Therefore, the temperature of the solution 19 is preferably maintained in the range between −33° C and room temperature by the use of a cooling apparatus as represented by a cooling coil 21 in FIG. 5 even when the ammonia concentration of the solution 19 does not exceed 14%. If the solution 19 is kept in a pressure vessel at a maximum pressure of 20 kg/cm$^2$, cooling may become unnecessary and the temperature may be raised to a maximum to 50° C. The sheet 10 is next passed through a dryer 14 to evaporate ammonia and water and enhance the adhesive strength of the precipitated silver chloride particles to the vinylon sheet 10. The thus produced bactericidal article 20 may be lightly washed with water and dried again if desired.

In general, this ammoniacal solution method gives the silver halide coatings 12 of higher adhesive strength than the foregoing method which uses nitrate and halide solutions.

EXAMPLE 1

A rolled belt of a non-woven vinylon cloth, which was 0.3 mm thick, 45 cm wide and weighing 70 g/m$^2$, was passed through a 15% aqueous solution of silver nitrate at room temperature. The belt was moved at such a speed that the immersion period in the solution was 1 minute. Then the silver nitrate coated belt was dried at 60° C by passing it through a 15 m long hot-air dryer for 30 minutes. Then the dried belt was passed through a 10% aqueous solution of sodium chloride at room temperature such that the immersion period was 1 minute. After that, the silver chloride coated belt was washed with flowing water and dried at 60° C.

The quantity of the silver chloride adhering to the resultant bactericidal cloth article was in the range between 1.20 and 1.25 g/1000 cm$^2$, where the area is the total area of the two sides of the cloth. The mean particle size of the adhering silver chloride was 0.05 microns.

An experiment was carried out to examine the adhesive strength of the silver chloride coatings with three samples prepared as in the above example using vinylon, polyester and rayon non-woven cloths, respectively. Test A was jumbling in a vessel for 24 hr by a stirrer, and Test B was vibration in a vibrating sieving apparatus for 24 hr. The results are shown in Table 1 in terms of the falling off rate of the silver chloride particles defined by $$\frac{W_0 - W_1}{W_0} \times 100 \, (\%),$$

where $W_0$ and $W_1$ are the weights of the silver chloride adhering to the sample before the test and after the test, respectively.

Table 1

|  | Falling off rate of AgCl particles | | |
| --- | --- | --- | --- |
|  | vinylon | polyester | rayon |
| Test A | 0.1 –0.6% | 2.5 – 3.3% | 0.2 – 0.6% |
| Test B | 0.3 – 0.9% | 4.5 –6.8% | 0.3 –0.8% |

The values for the vinylon cloth and rayon cloth are quite satisfactory, but the values for the polyester cloth pose a question about the practicality of the material. Also physical strength was examined with these three kinds of cloths after they were continuously immersed in water for several months. Both the vinylon and polyester cloths retained more than 95% of their respective original strength values even after 12 months, but the rayon cloth had weakened so that the strength test failed to give any numerical datum after only 3 months.

To examine the bactericidal power of the bactericidal cloth produced in Example 1, another experiment was carried out by the use of PJ-IRF type water purifiers manufactured by Matsushita Electric Industrial Co., Ltd. of Kadoma, Japan. In one water purifier, cut pieces of the bactericidal cloth were installed in a quantity to provide 1200 cm² total surface area, and the other purifier was provided with no bactericidal cloth. As seen in Table 2, the numbers of bacteria found in the treated water were surprisingly small where the bactericidal cloth was used, and also, the bactericidal cloth maintained its effectiveness substantially unchanged throughout a period of 180 days.

TABLE 2

Number of bacteria observed in the dechlorinated water (per ml). P-1 represents a water purifier having no bactericidal cloth, and P-2 a water purifier equipped with bactericidal cloth.

|  |  | (*1) 1 day | 7 days | 14 days | 30 days | 60 days | 90 days | 180 days |
|---|---|---|---|---|---|---|---|---|
| P - 1 | (*2) 0 – 5 ml | 0 | $8\times10^2$ | $9\times10^2$ | $2\times10^3$ | $1\times10^4$ | $3\times10^3$ | $5\times10^2$ |
|  | 100 – 105 ml | 0 | $2\times10^2$ | $3\times10^2$ | $4\times10^3$ | $3\times10^4$ | $4\times10^4$ | $7\times10^2$ |
|  | 200 – 205 ml | 0 | 56 | 91 | $2\times10^2$ | $2\times10^3$ | $2\times10^3$ | $1\times10^2$ |
|  | 500 – 505 ml | 0 | 0 | 3 | $1\times10^2$ | $3\times10^2$ | $1\times10^2$ | 23 |
| P - 2 | 0 – 5 ml | 0 | 33 | 42 | 64 | 5 | 24 | 11 |
|  | 100 – 105 ml | 0 | 4 | 3 | 4 | 21 | 16 | 7 |
|  | 200 – 205 ml | 0 | 0 | 6 | 8 | 8 | 18 | 3 |
|  | 500 – 505 ml | 0 | 0 | 0 | 1 | 0 | 0 | 0 |
| Cl⁻ concentration in supplied water (ppm) | | 20 | 18 | 20 | 22 | 20 | 18 | 17 |
| ambient temperature (° C) | | 25 | 25 | 25 | 25 | 25 | 25 | 25 |
| water temperature (° C) | | 10 | 14 | 16 | 16 | 18 | 21 | 29 |

(*1) days after beginning of the experiment
(*2) quantity of sample water taken from the purifier

EXAMPLE 2

The non-woven vinylon cloth of Example 1 was used. The belt-shaped cloth was passed through a silver ammine complex solution prepared by dissolving 3% by weight of silver chloride in 4% aqueous ammonia solution. The immersion was carried out at about 0° C and at atmospheric pressure, keeping the cloth belt in the complex solution for 1 minute. After removal from the solution, the cloth was air-dried, followed by a drying at 60° C in a dryer. The obtained bactericidal cloth had silver chloride coatings weighing about 1.5 g per 1000 cm² surface area.

What is claimed is:

1. A method of producing a sheet-formed bactericidal article for the sterilization of dechlorinated potable water in a water purifier, the article consisting of a cloth substrate and fine particles of silver chloride firmly deposited on the surfaces of the fiber filaments of the cloth substrate, the method comprising the steps of;
    soaking a non-woven cloth sheet of partially acetal-formed polyvinyl alcohol in an aqueous solution of silver nitrate in the concentration range from 1 to 20% by weight, the hydroxyl radicals in said partially acetal-formed polyvinyl alcohol having been subjected to partial condensation with an aldehyde to form acetal radicals such that the extent of the acetal formation is less than 50 mol% of polyvinyl alcohol;
    drying the soaked sheet to remove water; and
    soaking the dried sheet in an aqueous solution of sodium chloride in the concentration range from 1 to 20% by weight to convert said silver nitrate adhering to said sheet into silver chloride.

2. A method as claimed in claim 1, wherein said non-woven cloth sheet has a thickness between 0.01 and 5mm, the extent of the acetal formation being in the range between 5 and 30%.

3. A method of producing a sheet-formed bactericidal article for the sterilization of dechlorinated potable water in a water purifier, the article consisting of a cloth substrate and fine particles of silver chloride firmly deposited on the surfaces of the fiber filaments of the cloth substrate, the method comprising the steps of;
    preparing a silver amine complex solution by dissolving 0.1 to 20% by weight of silver chloride in an aqueous ammonia solution ranging in concentration from 1 to 14% by weight;
    soaking a non-woven cloth sheet of partially acetal formed polyvinyl alcohol in said solution, the hydroxyl radicals in said partially acetal-formed polyvinyl alcohol having been subjected to partial condensation with an aldehyde to form acetal radicals such that the extent of the acetal formation is less than 50 mol% of polyvinyl alcohol; and
    drying the soaked sheet to evaporate water and ammonia.

4. A method as claimed in claim 3, wherein the soaking step is carried out at atmospheric pressure keeping the temperature of said solution in a range between −33° C and room temperature.

5. A method as claimed in claim 3, wherein the soaking step is carried out at a pressure of 20 kg/cm² at the highest.

6. A method as claimed in claim 3 wherein said nonwoven cloth sheet has a thickness between 0.01 and 5mm, the extent of the acetal formation being in the range between 5 and 30 mol%.

* * * * *